US008431557B2

(12) United States Patent
Brennan et al.

(10) Patent No.: US 8,431,557 B2
(45) Date of Patent: Apr. 30, 2013

(54) TREATMENT OF MENOPAUSE-ASSOCIATED SYMPTOMS

(75) Inventors: John Brennan, Marietta, GA (US); Earl E. Sands, Kennesaw, GA (US); Rex Horton, Marietta, GA (US); Zurab Bebia, Smyrna, GA (US)

(73) Assignee: Besins Healthcare Luxembourg SARL, Grand-Duche du Luxembourg (LU)

( * ) Notice: Subject to any disclaimer, the term of this patent is extended or adjusted under 35 U.S.C. 154(b) by 0 days.

(21) Appl. No.: 13/408,760

(22) Filed: Feb. 29, 2012

(65) Prior Publication Data

US 2012/0157424 A1 Jun. 21, 2012

Related U.S. Application Data

(62) Division of application No. 11/783,889, filed on Apr. 12, 2007, now abandoned.

(60) Provisional application No. 60/791,456, filed on Apr. 13, 2006.

(51) Int. Cl.
| | | |
|---|---|---|
| A61K 31/565 | (2006.01) | |
| A61P 15/02 | (2006.01) | |
| A61P 9/00 | (2006.01) | |
| A61P 15/00 | (2006.01) | |
| A61P 5/30 | (2006.01) | |
| A61P 15/12 | (2006.01) | |

(52) U.S. Cl.
USPC .................................................. 514/182

(58) Field of Classification Search ........... 514/182
See application file for complete search history.

(56) References Cited

U.S. PATENT DOCUMENTS

| | | | |
|---|---|---|---|
| 5,891,462 | A | 4/1999 | Carrara |
| 2003/0027804 | A1 | 2/2003 | Van der Hoop |
| 2003/0181430 | A1 | 9/2003 | Gray et al. |
| 2004/0198706 | A1 | 10/2004 | Carrara et al. |
| 2006/0105041 | A1 | 5/2006 | Masini-Eteve |

FOREIGN PATENT DOCUMENTS

| | | |
|---|---|---|
| WO | WO 99/26631 A1 | 6/1999 |
| WO | WO 02/078682 A2 | 10/2002 |
| WO | WO-03/006027 | 1/2003 |
| WO | WO 2005/011618 A2 | 2/2005 |

OTHER PUBLICATIONS

Brennan et al.; "Serum Concentrations of 17β-Estradiol and Estrone After Multiple-Dose Administration of Percutaneous Estradiol Gel in Symptomatic Menopausal Women"; Therapeutic Drug Monitoring; 23:134-138 (2001).
Documed AG, "Sandrena® product information," (2 pgs.)(2001).
Simon et al; "Low Dose of Transdermal Estradiol Gel for Treatment of Symptomatic Postmenopausal Women"; Obstetrics & Gynecology; vol. 109, No. 3, pp. 588-596 (Mar. 2007).
Naunton et al.; "Estradiol gel: review of the pharmacology, pharmacokinetics, efficacy, and safety in menopausal women"; Menopause: The Journal of the North American Menopause Society; vol. 13, No. 3, pp. 517-527 (2006).
Watson Phrma Inc., "Alora® prescribing information," May 2005.
Novartis, "Vivelle® prescribing information," Aug. 2004.
Block, "Medicated Topicals," Remington: The Science and Practice of Pharmacy, Gennaro, ed., 20th ed., pp. 836-845, and 917-918, 2000.
U.S. Department of Health and Human Services, Food and Drug Administration, Center for Drug Evaluation and Research (CDER), "Guidance for Industry—Estrogen and Estrogen/Progestin Drug Products to Treat Vasomotor Symptoms and Vulvar and Vaginal Atrophy Symptoms—Recommendations for Clinical Evaluation," pp. 1-10, Jan. 2003.
Chiang et al., "Bioavailablity accessment of topical delivery systems: Effect of vehicle evaporation upon in vitro delivery of minoxidil from solution formulations," International Journal of Pharmaceutics, vol. 55, pp. 229-236, 1989.
Novartis, Vivelle-Dot® prescribing information, NDA 20-538/S-019, pp. 3-30 (approved May 2002).
Office Action issued on Sep. 29, 2011 by the Examiner in U.S. Appl. No. 11/783,889 (US 2007/0254036).
Office Action issued on Dec. 23, 2010 by the Examiner in U.S. Appl. No. 11/783,889 (US 2007/0254036).
Office Action issued on Jun. 1, 2010 by the Examiner in U.S. Appl. No. 11/783,889 (US 2007/0254036).
Office Action issued on Sep. 16, 2009 by the Examiner in U.S. Appl. No. 11/783,889 (US 2007/0254036).
Office Action issued on May 15, 2009 by the Examiner in U.S. Appl. No. 11/783,889 (US 2007/0254036).

*Primary Examiner* — Jeffrey S. Lundgren
*Assistant Examiner* — Sara E Townsley
(74) *Attorney, Agent, or Firm* — Foley & Lardner LLP

(57) ABSTRACT

Described are estradiol-containing pharmaceutical compositions and, and methods using the same to alleviate menopause-related symptoms, such as hot flushes, by topically administering estradiol at low effective doses.

12 Claims, No Drawings

TREATMENT OF MENOPAUSE-ASSOCIATED SYMPTOMS

CROSS-REFERENCE TO RELATED APPLICATION

This application is a divisional of U.S. application Ser. No. 11/783,889, filed Apr. 12, 2007, which claims priority to U.S. Provisional Application Ser. No. 60/791,456, filed Apr. 13, 2006, both of which are incorporated herein by reference.

FIELD OF THE INVENTION

The present invention relates to estradiol-containing pharmaceutical compositions and gels, and to methods using the same. More particularly, the present invention relates to alleviating menopause-related symptoms by topically administering estradiol at low effective doses.

BACKGROUND

Menopause is very often associated with symptoms such as hot flushes. Such symptoms have a major negative impact on post-menopausal female life quality.

Estradiol (17-beta estradiol) is the most potent naturally occurring estrogen in mammals, in which it is formed by the ovary, placenta, testis, and possibly the adrenal cortex. Administering estradiol has proven effective for alleviating certain menopause-associated symptoms, in particular hot flushes. However, due to increasingly important patient safety requirements, it is highly desirable to provide compositions, methods and uses effective for alleviating such symptoms without overestimating the required therapeutic dose.

In *Serum concentrations of 17beta-estradiol and estrone after multiple-dose administration of percutaneous estradiol gel in symptomatic menopausal women*, Brennan J J, Lu Z, Whitman M, Stafiniak P, van der Hoop R G. Ther Drug Monit. 2001 April; 23(2):134-8, the authors used a hydro-alcoholic gel containing estradiol. They found that daily topical administration of a 0.75 mg dose of estradiol (1.25 g of said gel per day) resulted in an elevation in the serum estradiol level, reaching values compatible with a relief in vasomotor symptoms. Further, the authors indicated that a lower estradiol dose did not achieve similar serum levels, and thus was not expected to be consistently therapeutic in reducing vasomotor symptoms.

SUMMARY

Described herein is a method of alleviating at least one menopause-associated symptom in a female patient in need thereof, comprising topically administering to said patient an amount of a composition comprising estradiol effective to administer an estradiol dose of about 0.25-0.42 mg/day. In some embodiments, the estradiol dose is about 0.35-0.40 mg/day, and in particular embodiments the estradiol dose is about 0.375 mg/day.

In some embodiments, the menopause-associated symptom is selected from the group consisting of vasomotor symptoms, vulvar atrophy, vaginal atrophy, and combinations thereof. In particular embodiments the menopause-associated symptom is hot flushes. In some embodiments, the method is effective to achieve at least one effect selected from the group consisting of decreasing the severity of vasomotor symptoms, decreasing the frequency of vasomotor symptoms, decreasing the severity of vulvar atrophy, decreasing the severity of vaginal atrophy, and combinations thereof.

Also described are compositions useful, for example, in these methods. In some embodiments, the composition is a hydroalcoholic gel that comprises (i) about 0.025-0.035% (w/w) estradiol, (ii) about 0.1-1.5% (w/w) gelling agent, (iii) about 30-50% (w/w) C2-C6 alcohol, and (iv) water. In some embodiments, the gelling agent comprises at least one polyacrylic acid, such as a carbomer, for example, Carbopol® 980, Carbopol® 934P, Carbopol® 1342, Carbopol® 1382, and mixtures thereof. In a particular embodiment, the composition comprises (i) about 0.03% (w/w) estradiol, (ii) about 0.5-1% (w/w) polyacrylic acid polymer, (iii) about 40% (w/w) absolute ethanol, and (iv) water.

In some embodiments, the composition is a hydroalcoholic gel that comprises (i) about 0.03% (w/w) estradiol; and (ii) about 40% (w/w) absolute ethanol, and has a Brookfield viscosity at 20° C. of between 30-120 Pa·s., such as 35-100 Pa·s., and 50-60 Pa·s.

Also described are unit dose compositions suitable for topical administration, comprising about 0.25-0.42 mg estradiol, including unit dose compositions comprising about 0.35-0.40 mg estradiol, and unit dose compositions comprising about. 0.375 mg estradiol.

Methods comprising administering the compositions also are described.

DETAILED DESCRIPTION

According to the present invention, it has been surprisingly and unexpectedly found that topical doses of estrogen lower than 0.75 mg/day alleviate menopause-related symptoms. Thus, overcoming a strong prejudice in the art, embodiments of the present invention provide lower effective doses of estradiol for alleviating menopause-associated symptoms, in particular hot flushes.

In some embodiments, the present invention provides a use of estradiol in the manufacture of a medicament for alleviating at least one menopause-associated symptom.

In other embodiments, the present invention provides the use of estradiol in the manufacture of a medicament for topically administering a lower dose of estradiol, wherein said medicament is for alleviating at least one menopause-associated symptom.

In accordance with one embodiment, there is provided a composition or medicament suitable for topical administration that comprises estradiol.

In some embodiments, the composition or medicament is formulated to provide topical/transdermal delivery of estradiol.

In accordance with another embodiment, there is provided a method of alleviating at least one menopause-associated symptom. In some embodiments, the method comprises topically administering a composition or medicament suitable for topical administration that comprises estradiol, such as a composition or medicament formulated to provide topical/transdermal delivery of estradiol.

In some embodiments, the composition or medicament, which may be effective for alleviating at least one menopause-associated symptom, is formulated for topically administering an estradiol dose of about 0.25-0.42 mg/day, including about 0.35-0.40 mg/day, such as about 0.375 mg/day of estradiol. For example, said medicament may be formulated for administering a dose of about 0.25-0.42, about 0.26-0.42, about 0.27-0.42, about 0.28-0.42, about 0.29-0.41, about 0.30-0.41, about 0.31-0.41, about 0.32-0.40, about 0.33-0.40, about 0.34-0.40, about 0.35-0.40, about 0.355-0.395, about 0.36-0.39, about 0.365-0.385, about 0.37-0.38, or about 0.375 mg/day of estradiol, such as 0.25-0.42, 0.26-

0.42, 0.27-0.42, 0.28-0.42, 0.29-0.41, 0.30-0.41, 0.31-0.41, 0.32-0.40, 0.33-0.40, 0.34-0.40, 0.35-0.40, 0.355-0.395, 0.36-0.39, 0.365-0.385, 0.37-0.38, or 0.375 mg/day of estradiol.

Therapeutic Methods

As noted above, the present invention provides a method for alleviating at least one menopause-associated symptom in a female subject. In some embodiments, said method comprises topically administering a composition comprising a low dose of estradiol. As used herein, "low dose" indicates that the topical administration is such that about 0.25-0.42 mg/day, including about 0.35-0.40 mg/day, such as about 0.375 mg/day of estradiol is administered onto the subject's skin. For example, said topical administration can be such that a dose of about 0.25-0.42, about 0.26-0.42, about 0.27-0.42, about 0.28-0.42, about 0.29-0.41, about 0.30-0.41, about 0.31-0.41, about 0.32-0.40, about 0.33-0.40, about 0.34-0.40, about 0.35-0.40, about 0.355-0.395, about 0.36-0.39, about 0.365-0.385, about 0.37-0.38, or about 0.375 mg/day of estradiol is administered onto the subject's skin, such as 0.25-0.42, 0.26-0.42, 0.27-0.42, 0.28-0.42, 0.29-0.41, 0.30-0.41, 0.31-0.41, 0.32-0.40, 0.33-0.40, 0.34-0.40, 0.35-0.40, 0.355-0.395, 0.36-0.39, 0.365-0.385, 0.37-0.38, or 0.375 mg/day of estradiol administered onto the subject's skin.

Said topical administration can comprise one or two (or more) applications per day, such as one topical application per day. In alternative embodiments, the topical administration is effected less frequently than once per day, such as on alternate days, such that the average daily dose is within the above-described ranges.

According to one aspect, the composition or medicament is applied on healthy, clean and dry skin, e.g. to the shoulder, or to the arm, e.g. to the external part of the arm, or from the wrist to the shoulder; thigh or leg. Alternatively, the composition or medicament may be applied onto the abdomen, the thigh(s) or the lumbar area. Other suitable administration sites also are encompassed.

In one aspect of the invention, said menopause-associated symptom is selected from:
vasomotor symptoms,
vulvar atrophy,
vaginal atrophy, and
combinations thereof.

Vasomotor symptoms are known in the art, and include all hot flushes, such as mild hot flushes, moderate hot flushes, moderate to severe hot flushes, and severe hot flushes. Hot flushes generally refer to a heat or warmth sensation, generally in the upper body, such as the face and/or neck and/or chest. They are typically very sudden and/or very brief, and may be accompanied by a rapid heartbeat and blood vessel dilatation. The duration of such symptoms varies, and may typically be from two to thirty minutes on each occasion. The frequency also varies, e.g. symptoms may be repeated a few times each week or up to a dozen times a day and more. Amongst hot flushes, also the intensity may vary:
mild hot flushes include a sensation of heat without perspiration;
moderate hot flushes include a sensation of heat with perspiration, but the subject is able to continue with her activity;
severe hot flushes include a sensation of heat with sweating, sufficiently severe to result in discontinuation of activity.

Vulvar and vaginal atrophy are known in the art, and may include vaginal pain associated with sexual activity; bleeding associated with sexual activity; dysuria; dryness, irritation, itching, and/or burning in and around the vaginal area; and combinations thereof.

By 'alleviating a symptom', it is herein meant providing relief against said symptom, e.g. lessening the intensity, severity (including duration), and/or frequency/occurrence thereof.

Advantageously, in accordance with some embodiments, topically administering estradiol at the doses according to the invention, e.g., administering the compositions and medicaments described herein, results in at least one effect selected from:
a decrease in the severity of vasomotor symptoms,
a decrease in the frequency of vasomotor symptoms,
a decrease in the severity of vulvar atrophy,
a decrease in the severity of vaginal atrophy,
and combinations thereof.

According to one aspect, beneficial effects comprise a decrease in the severity of vasomotor symptoms that is observed after treatment, such as after 12, 10, 8, 6, 4, or 2 weeks of treatment with the doses and methods according to the invention.

According to another aspect, beneficial effects comprise a decrease in the frequency of vasomotor symptoms that is observed after treatment, such as after 12, 10, 8, 6, 4, or 2 weeks of treatment with the doses and methods according to the invention.

According to another aspect, beneficial effects comprise a decrease in the severity of moderate to severe hot flushes that is observed after treatment, such as after 12, 10, 8, 6, 4 or 2 weeks of treatment (or less) with the doses and methods according to the invention.

According to another aspect, beneficial effects comprise a decrease in the frequency of moderate to severe hot flushes that is observed after treatment, such as after 12, 10, 8, 6, 4 or 2 weeks of treatment (or less) with the doses and methods according to the invention.

According to another aspect, beneficial effects comprise a decrease in the severity of vulvar and/or vaginal atrophy that is observed after treatment, such as after 12, 10, 8, 6, 4 or 2 weeks of treatment (or less) with the doses and methods according to the invention.

Further beneficial effects obtained according to specific embodiments of the invention may include an improvement in at least one criterion selected from the group consisting of
Menopause Rating Scale (MRS): a scale for measuring health-related quality of life.
Menopause-Specific Quality of Life Questionnaire (MN-QOL): for assessing vasomotor, physical, psychological and sexual criteria.

Those skilled in the art would know how to provide a composition or medicament suitable for topically administering the estradiol at doses according to the invention. Examples of suitable compositions and medicaments are described below.

Generally speaking, the volume, the concentration, and the number of daily applications of the composition/medicament are such that the dose of estradiol administered onto the subject's skin is about 0.25-0.42, about 0.26-0.42, about 0.27-0.42, about 0.28-0.42, about 0.29-0.41, about 0.30-0.41, about 0.31-0.41, about 0.32-0.40, about 0.33-0.40, about 0.34-0.40, about 0.35-0.40, about 0.355-0.395, about 0.36-0.39, about 0.365-0.385, about 0.37-0.38, or about 0.375 mg/day, such as 0.25-0.42, 0.26-0.42, 0.27-0.42, 0.28-0.42, 0.29-0.41, 0.30-0.41, 0.31-0.41, 0.32-0.40, 0.33-0.40, 0.34-0.40, 0.35-0.40, 0.355-0.395, 0.36-0.39, 0.365-0.385, 0.37-

0.38, or 0.375 mg/day. Thus, for instance, for applications of the same volume of the same composition or medicament:

Dose=Volume×Concentration×Number, wherein
Dose: estradiol dose administered to skin of subject per day,
Concentration: estradiol concentration of the composition or medicament,
Volume: volume of topical composition administered per application,
Number: number of applications per day.

In another aspect of the invention, the dosage regimen may make use of a treatment phase with a loading dose, followed by a phase with a maintenance dose. Thus, the patient might start the treatment with a short period (e.g. 1, 2, 3 or 4 weeks) using a higher dose (loading phase), and then continue with a lower dose (maintenance phase). For example, the patient might start with a loading phase with doses higher than the doses of the invention, and then carry on with the low doses of the invention. Alternatively, the patient may initiate with a loading phase with doses according to the invention, and then switch to even lower doses. Such phases may be cycled. In another aspect, the patient might start with administration steps once or twice a day on a short period (e.g. 1, 2, 3 or 4 weeks), and then switch to a regimen at lower doses, with an administration step every other day. The daily dose would then be the average dose per day. Also encompassed are other dosing regimens that may be tailored to meet a specific patient's needs according to methods known in the art.

Thus, the present invention provides a method for alleviating a menopause-associated symptom in a female subject, comprising topically administering a composition comprising an estrogen (such as estradiol). In some embodiments, said estrogen is administered onto the subject's skin in an amount which has an estrogenic potency equivalent to about 0.25-0.42 mg/day, including about 0.35-0.40 mg/day, or about 0.375 mg/day of estradiol, such as 0.25-0.42 mg/day, 0.35-0.40 mg/day, or 0.375 mg/day of estradiol. For example, the invention provides a method of alleviating at least one menopause-associated symptom in a female patient in need thereof, comprising topically administering to said patient an amount of a composition comprising estradiol effective to administer an estradiol dose of about 0.25-0.42 mg/day, including about 0.35-0.40 mg/day, or about 0.375 mg/day of estradiol.

Compositions and Medicaments

The invention also provides compositions and medicaments comprising an estrogen (such as estradiol). In some embodiments, the compositions and medicaments are formulated for topical administration. In specific embodiments, the compositions and medicaments are formulated for the topical/transdermal delivery of an estrogen (such as estradiol) in daily amounts having the estrogenic potency equivalent to about 0.25-0.42 mg/day, including about 0.35-0.40 mg/day, or about 0.375 mg/day of estradiol, such as 0.25-0.42 mg/day, 0.35-0.40 mg/day, or 0.375 mg/day of estradiol. In some embodiments, the composition or medicament comprises an amount of estradiol effective to administer an estradiol dose of about 0.25-0.42 mg/day. In some embodiments, such a medicament is useful for alleviating at least one menopause-associated symptom.

Advantageously according to some embodiments of the invention, estradiol can be provided in a gel composition. In one aspect, the composition or medicament according to the invention is an estradiol-containing hydro-alcoholic gel. Said composition or medicament may comprise estradiol, a gelling agent, an alcohol, and water.

Estradiol

As noted above, the invention provides compositions and medicaments comprising estradiol.

In one aspect, the composition or medicament may comprise about 0.025-0.035%, including about 0.026-0.034%, about 0.027-0.033%, about 0.028-0.032%, about 0.0285-0.0315%, about 0.029-0.031%, about 0.0295-0.0305%, or about 0.03% of estradiol, such as 0.025-0.035%, 0.026-0.034%, 0.027-0.033%, 0.028-0.032%, 0.0285-0.0315%, 0.029-0.031%, 0.0295-0.0305%, or 0.03% of estradiol.

(Unless otherwise stated, percentages (%) refer to amounts by weight based upon total weight of the composition (% (w/w)).)

Said estradiol may be of natural origin, or may result from a hemisynthesis or synthesis process. Estradiol can be provided as anhydrous estradiol, as well as hydrate of estradiol, e.g. estradiol semi-hydrate. (The given percentages refer to the amount of anhydrous estradiol.) Alternatively, said estradiol may be substituted by another estrogen. Estrogens are known, and those skilled in the art are aware of the respective relative potency (estrogenic activity) of estrogens comparatively to estradiol. The ratios can then be used to convert the doses of estradiol according to the invention into the equivalent amount of a given estrogen corresponding to an equivalent estrogenic potency. Examples of estrogens include estriol, estrone, ethynil estradiol, as well as derivatives thereof, including conjugated and esterified estrogens (e.g. acetate, cypionate and valerate derivatives of estrogens).

Gelling Agent

In some embodiments, the composition or medicament may comprise a gelling agent.

In one aspect, the composition or medicament may comprise about 0.5-1.5%, including about 0.6-1.4%, about 0.7-1.3%, about 0.8-1.2%, about 0.85-1.15, %, about 0.9-1.1%, about 0.95-1.05%, or about 1% of a gelling agent, such as 0.5-1.5%, 0.6-1.4%, 0.7-1.3%, 0.8-1.2%, 0.85-1.15, %, 0.9-1.1%, 0.95-1.05%, or 1% of a gelling agent. In some such embodiments, the gelling agent is a polyacrylic acid polymer, such as Carbopol® 934P.

In another aspect, the composition or medicament may comprise about 0.1-0.9%, including about 0.2-0.8%, about 0.3-0.7%, about 0.4-0.6%, about 0.45-0.55%, or about 0.5% of a gelling agent, such as 0.1-0.9%, 0.2-0.8%, 0.3-0.7%, 0.4-0.6%, 0.45-0.55%, or 0.5% of a gelling agent. In some such embodiments, the gelling agent is a polyacrylic acid polymer such as Carbopol® 980P.

Gelling agents are known in the art. The term 'gelling agent' generally refers to a compound, possibly of polymeric nature, having the capacity to gel when contacted with a specific solvent, e.g. water. Gelling agents make it possible to increase the viscosity of the pharmaceutical compositions according to the invention, but may also act as solubilizing agents. Examples of gelling agents include anionic polymers such as acrylic acid-based polymers (including polyacrylic acid polymers, e.g. CARBOPOL® by B.F. Goodrich Specialty Polymers and Chemicals Division of Cleveland, Ohio), cellulose derivatives, poloxamers and poloxamines. More precisely, gelling agents optionally may be selected from carbomers or acrylic acid-based polymers, e.g. Carbopol® 980 or 940, 981 or 941, 1382 or 1382, 5984, 2984, 934 or 934P (Carbopol® are usually polymers of acrylic acid crosslinked with allyl sucrose or allylpentaerythritol), Pemulen TR1® or TR2®, Ultrez, Synthalen CR, etc.); cellulose derivatives such as ethylcelluloses, hydroxypropylcelluloses, hydroxyethylcelluloses, hydroxypropylmethylcelluloses (HPMC), carboxymethylcelluloses (CMC), etc.; poloxamers or polyethylene-polypropylene copolymers such as Lutrol® grade 68 or 127, poloxamines and other gelling agents such as chitosan, dextran, pectins, and natural gums. Any of these gelling agents, or any other pharmaceutically acceptable gelling agent, may be used alone or in combination in the composition or medicament according to the invention. Selection of a suitable gelling agent may be guided by principles known in the art, for example, taking into account the pH of the composition according to the invention and the desired viscosity. Carbopol® 980 and Carbopol 934P® are examples of gelling agents suitable for use in the context of the present invention.

In some embodiments, the gelling agent is reacted with a further ingredient (such as a neutralizer), in order to reach the desired viscosity. For example, when using a polyacrylic acid polymer as a gelling agent, a gel texture may be obtained by neutralizing said polyacrylic acid polymer with a base. Suitable bases include triethanolamine, tromethamine, sodium hydroxide, ammonium hydroxide, potassium hydroxide, arginine, and aminomethylpropanol. The skilled person knows how to choose a suitable neutralizer for a given polymer, and also knows how to adjust the ratio between the gelling agent and the neutralizer. When using a polyacrylic acid polymer, triethanolamine is a suitable neutralizer. For example, said composition or medicament may comprise about 0.5% of Carbopol 980® or 1% of Carbopol 934P®. A suitable texture (viscosity) may be obtained by neutralizing, respectively, with about 0.5% or 1% of triethanolamine.

Alcohol

In some embodiments, the composition or medicament may comprise alcohol.

In one aspect, the composition or medicament may comprise about 30-50%, including about 32-48%, about 33-47%, about 34-46%, about 35-45%, about 36-44%, about 37-43%, about 38-42%, about 39-41%, or about 40% of a C2-C6 alcohol, such as 30-50%, 32-48%, 33-47%, 34-46%, 35-45%, 36-44%, 37-43%, 38-42%, 39-41%, or 40% of a C2-C6 alcohol. C2-C6 alcohols are known in the art. Such alcohols encompass ethanol, propanol, isopropanol (propan-2-ol), n-propanol (propan-1-ol), butanol, butan-1-ol, butan-2-ol, ter-butanol, pentanols, hexanols. A suitable C2-C6 alcohol is ethanol.

Penetration Enhancers

The composition or medicament optionally may comprise a penetration enhancer. Penetration enhancers are known in the art. A 'penetration enhancer' is generally an agent known to accelerate the delivery of the drug or active principle through the skin. These agents also have been referred to as penetration accelerants, adjuvants, and absorption promoters. This class of agents includes those with diverse mechanisms of action including those which have the function of improving the solubility and diffusibility of the drug, and those which improve transdermal absorption by changing the ability of the stratum corneum to retain moisture, softening the skin, improving the skin's permeability, acting as penetration assistants or hair-follicle openers or changing temporarily the state of the skin such as the boundary layer.

The compositions and medicament according to the invention optionally may include one or several penetration enhancers. Advantageously, the presence of a penetration enhancer allows finely tuning the serum levels and other pharmacokinetics parameters. Those skilled in the art would know how to select a suitable penetration enhancer, and the corresponding suitable contents in the composition/medicament. Such penetration enhancer within the context of the present invention can be, for example, a functional derivative of a fatty acid, which includes isosteric modifications of fatty acids or non-acidic derivatives of the carboxylic functional group of a fatty acid or isosteric modifications thereof. In one embodiment, the functional derivative of a fatty acid is an unsaturated alkanoic acid in which the —COOH group is substituted with a functional derivative thereof, such as alcohols, polyols, amides and substituted derivatives thereof. The term "fatty acid" means a fatty acid that has four (4) to twenty-four (24) carbon atoms. Non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; glycol ethers including diethylene glycol monoethyl ether; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; pyrrolidones and N-alkylpyrrolidone; terpenes; hydroxyacids; urea; essential oils; and mixtures thereof. Specific examples include propylene glycol, oleic acid, glycerine, lactic acid, leucic acid, ethyl glycolic acid. All of these penetration enhancers can be used either alone or in combination, e.g. in combinations of two or three (or more) different penetration enhancers.

Other Optional Components

In some embodiments, the composition or medicament of the invention optionally may comprise one or more other usual pharmaceutical additives, including salt(s), emollient(s), stabilizer(s), antimicrobial(s), fragrance(s), and/or propellant(s). Said composition or medicament may also optionally include at least one further active ingredient, e.g. another hormone.

Water

In some embodiments the composition or medicament may comprise water. In one aspect, the composition or medicament comprises water, in a quantity sufficient (q.s.) to reach 100%.

In one embodiment, the composition or medicament comprises about:
  0.025-0.035% of estradiol,
  0.1-1.5% of a gelling agent,
  30-50% of a C2-C6 alcohol,
  q.s. water.

In another embodiment, the composition or medicament comprises about;
  0.03% of estradiol,
  0.5-1% of a polyacrylic acid polymer (for instance 0.5% Carbopol
    980®, which may be neutralized with 0.5% triethanolamine; as a further example, 1% Carbopol 934P neutralized with 1% triethanolamine)
  40% of absolute ethanol,
  q.s. water.

In one aspect, the composition or medicament comprises about:
  0.03% of estradiol,
  40% of absolute ethanol,
and has a Brookfield viscosity at 20° C. of between about 30-120, including about 35-110, about 35-100, about 35-90, about 35-80, about 40-70, or about 50-60 Pa·s., such as a Brookfield viscosity at 20° C. of between 30-120, 35-110, 35-100, 35-90, 35-80, 40-70, or 50-60 Pa·s.

In one aspect, the composition or medicament has a Brookfield viscosity at 20° C. of between about 30-70, including about 31-69, about 32-68, about 33-67, about 34-66, or about 35-65 Pa·s., including a Brookfield viscosity at 20° C. of between 30-70, 31-69, 32-68, 33-67, 34-66, or 35-65 Pa·s.

In another aspect, the composition or medicament has a Brookfield viscosity at 20° C. of between about 40-120, including about 42-116, about 44-112, about 46-108, about 48-104, or about 50-100 Pa·s., such as 40-120, 42-116, 44-112, 46-108, 48-104, or 50-100 Pa·s.

Said Brookfield viscosity at 20° C. may be measured as follows: a sample of the composition is equilibrated at 20° C., e.g. in a water bath. The viscosity is measured using a TC needle in an RVT BROOKFIELD viscosimeter at 5 rpm.

Method of Manufacture

The compositions or medicaments described herein may be obtained by methods known in the art. An exemplary method of making a specific embodiment is described below:

Estradiol is dissolved, e.g. by mixing or stirring, in an alcohol, such as a C2-C6 alcohol. Water is added, again with mixing or stirring. The gelling agent is then added, again with stirring or mixing. The neutralizer (e.g. a base) is then added under stirring. The composition can then be packaged in a suitable package, such as described below.

Packaging/Dispensing

According to another embodiment, the composition or medicament may be provided in a dose packet, unit dose packet or multiple dose packet. Advantageously, such packaging renders application and dosage easier for a patient. Accordingly, these forms of packaging can reflect the schedule of application. Patient compliance can be greatly improved by providing the composition or medicament as individual unit dose packets, each packet corresponding to one administration step. For example, said unit dose packet may be a sachet, which can be torn open on one side or in one corner. One skilled in the art would know how to provide such sachets. For instance, the sachet may be of a mono- or multi-layered material, e.g. a multi-foil material. The sachet may itself contain an inner layer. Said sachet may advantageously be in the form of a stick pack, with sealings at both ends of the sachet and a longitudinal seal parallel to the main axis of the sachet. For example, the materials used in the multifoil material may include PET and/or aluminium and/or at least one polyolefin like polyethylene (PE), and combinations thereof. It may be a PET/Aluminium/PE multifoil with polyethylene (PE) in the inner layer. Also encompassed are other dose packets, including other unit dose packet designs and multiple dose packets.

According to another embodiment, there is provided a dispenser, e.g. a bottle or the like, optionally with metered hand pump or valve, containing said composition or medicament. Such dispensers allow for improved patient compliance, as the dispenser may be designed so as to precisely provide the desired dose according to the invention. For example, the dispenser may be an airless system with a metered pump and a plastic bottle containing a multifoil pouch. The pump/valve is advantageous in that it prevents presence of gas inside the container. The pouch may comprise a layer of plastic (for example a polyolefin like PE) co-extruded with another layer made of sealed PET/Aluminium/PE. Also encompassed are other dispensers, including other metered dose dispensers.

According to another aspect, said packet may be a tube, provided as a kit of parts with means for precisely metering the amount of medicament or composition. For example, the tube (e.g. for dispensing a gel) may be provided with a metering ruler or container, allowing the patient to measure the required amount (e.g. volume) of composition or gel to be administered.

According to one embodiment, said packets or dispensers can be accompanied by a notice/leaflet giving instructions for the use thereof.

Also encompassed are other packaging and dispensing devices.

Combination Therapies

The present invention can also be used in "combination therapy" with another pharmaceutically active agent, such as another hormone or steroid, for example progesterone or a progestagen. Progestagens are hormones which generally produce effects similar to progesterone, which is the only natural progestagen. Said progestagen may be a progestin. A progestin is a synthetic progestagen. Progestins include C19 and C21 progestagens. Examples thereof include norethindrone, norethindrone acetate, cyproterone, cyproterone acetate, dydrogesterone, medroxyprogesterone, medroxyprogesterone acetate, chlormadinone acetate, megestrol, megestrol acetate, promegestone, norelgestromin ethynodiol diacetate, drospirenone, norethisterone, (levo)norgestrel, lynestrenol, desogestrel, norgestimate, gestodene dimethisterone, 17alpha-Hydroxyprogesterone caproate, lynoestrenol, norethynodrel, norgestrel, northindrone acetate and tibolone.

The skilled person would know how to administer such progestagen (administration route, dosage, etc). Said progestagen may be provided separately (e.g. via the oral route) or as a further ingredient of the topical composition.

Some advantages of the invention will become apparent from the following examples, which are given below as mere illustrations, and are non limitative.

The skilled person will appreciate that the present invention can incorporate any number of the specific features described above.

All citations mentioned herein are hereby incorporated by reference in their entirety.

Other embodiments of the present invention not presented here, but which are obvious to those skilled in the art, are within the scope and the spirit of the present invention. The practice of the present invention will employ, unless otherwise indicated, conventional techniques of pharmacology and pharmaceutics, which are within the skill of the art.

EXAMPLE

Efficacy Study Comparing Topical Estradiol Doses of 0.27 mg and 0.375 mg/Day with Placebo in the Treatment of Menopause-Associated Symptoms Methodology This study was a multi-centred, double-blind, placebo-controlled, parallel group comparison. A total of 351 subjects were enrolled at 78 sites in the United States. The subjects were females 45 to 65 years of age, naturally or surgically menopausal, and had a minimum of 7 to 8 severe hot flushes/day or an average of ≧50 moderate and/or severe hot flushes per week, as verified during the 2-week Pre-Treatment Phase, prior to randomization.

A two-week, medication free, Pre-Treatment Phase was used to determine subject vasomotor symptoms. Efficacy assessments included the number and intensity of hot flushes per day, and severity of vulvar and vaginal atrophy symptoms. This study uses a topical gel having the following formulation (w/w):

0.03% estradiol,
1% Carbopol® 934P, neutralized with 1% triethanolamine,
40% absolute ethanol,
q.s. water.

This typically has a Brookfield viscosity at 20° C. of between 30-120 Pa·s.

Subjects were randomized to receive daily:
0.9 g of gel, corresponding to a dose of 0.27 mg estradiol,
1.25 g of gel, corresponding to a dose of 0.375 mg estradiol, or
placebo gel.

The three treatment groups comprised the following dosages:

A 0.375 mg dose (1.25 g of gel @ 0.03%) applied to one arm and 0.9 g of placebo gel applied on the other arm once daily for 12 weeks;

A 0.27 mg dose (0.9 g of gel @ 0.03%) applied to one arm and 1.25 g of placebo gel applied on the other arm once daily for 12 weeks; and 0.9 g of placebo gel applied to one arm and 1.25 g of placebo gel applied on the other arm once daily for 12 weeks.

The Treatment Phase was 12 weeks. A pre-treatment period of 2 weeks was used to initially evaluate each subject's vasomotor symptoms.

All data were analyzed using the approach of Observed Cases (OC).

Statistical Methods

For all continuous primary and secondary efficacy parameters, descriptive statistics tables and 2-way ANCOVA with fixed factors treatment and centre, and baseline value as covariate were provided. The interaction of treatment and centre was investigated using 2-way ANCOVA with fixed factors treatment, centre, and treatment-by-centre interaction with baseline value as covariate. To control the Type-I error rate, a step-down procedure using contrasts was performed to compare each treatment group to the placebo group. First, the group with the 0.375 mg dose was compared against placebo at the $\alpha=0.05$ level (2-sided). If the null hypothesis was rejected, the group with the 0.27 mg dose was compared to placebo at the $\alpha=0.05$ level (2-sided). Graphs were used to characterize the dose response. If the assumptions of the model were not met, then van Elteren's test with centre as the stratification variable was used in the step-down procedure. For categorical data, Fisher's exact test was used to compare treatment groups.

Study Variables

The study assessed the following variables:

Mean change in frequency of moderate to severe vasomotor symptoms from baseline to Week 4;

Mean change in frequency of moderate to severe vasomotor symptoms from baseline to Week 12;

Mean change in severity of moderate to severe vasomotor symptoms from baseline to Week 4;

Mean change in severity of moderate to severe vasomotor symptoms from baseline to Week 12;

Mean change in frequency of moderate-to-severe hot flushes at each week;

Mean change in severity of moderate-to-severe hot flushes at each week;

Mean change from baseline to Week 12 in the moderate to severe symptom of vulvar and vaginal atrophy that has been identified by the subject as being the most bothersome to her (vaginal pain, dryness, irritation/itching, bleeding, dysuria);

The baseline value was defined as the daily average of moderate to severe hot flushes during the 2 Pre-Treatment Phase weeks. The "daily average" was calculated from "the mean across the reported days at each week or at Pre-Treatment Phase weeks. If only mild hot flushes were reported on any day, the moderate to severe hot flush value for the subject on that day was zero. If less than 10 days of data were available for the baseline period, the baseline daily average was considered missing.

Severity of moderate to severe vasomotor symptoms was defined as (2*number of moderate hot flushes+3*number of severe hot flushes)/total number of moderate and severe hot flushes.

As with frequency, if less than 10 days of data were available for the baseline period, the baseline severity was considered missing.

Assessment of Hot Flushes (Vasomotor Symptoms)

On a daily basis, the subject recorded the number of hot flushes and rated the intensity of each based on a four-point scale as follows:

0 (none)
1 (mild) Sensation of heat without perspiration
2 (moderate) Sensation of heat with perspiration, but the subject was able to continue with her activity
3 (severe) Sensation of heat with sweating, sufficiently severe to result in discontinuation of activity Assessment of Vulvar and Vaginal Atrophy Symptom Severity The severity of symptoms of vulvar and vaginal atrophy (vaginal pain associated with sexual activity, dryness, irritation/itching, bleeding associated with sexual activity, or dysuria) that was identified by the subject as moderate to severe and most bothersome was assessed at Week 1, Week 12, or Early Termination using the following rating scale:

| 0 | None |
| 1 | Mild |
| 2 | Moderate |
| 3 | Severe |

Plasma Concentrations of Estradiol and Unconjugated Estrone

A single 10 mL sample of whole blood was collected at baseline, Weeks 4, 8, and 12. To eliminate the possibility of sample contamination, only the specimens obtained from the arm not used for estradiol application were reported. Plasma concentrations of estradiol and unconjugated estrone were analyzed using HPLC with MS/MS detection.

Example 1

Frequency and Severity of Vasomotor Symptoms at weeks 4 and 12

The primary analysis of observed cases data for frequency and severity of moderate to severe hot flushes at Weeks 4 and 12 showed a statistically significant difference between the 0.375 mg dose and placebo for all 4 criteria. Therefore, the 0.375 mg dose was shown to be efficacious vs. placebo (See Table 1).

TABLE 1

P-values - Moderate to Severe Hot Flushes
at Week 4 and 12 Observed Case Analysis

| Comparison | Frequency of Moderate to Severe Hot Flushes | | Severity of Moderate to Severe Hot Flushes | |
|---|---|---|---|---|
| | Week 4 | Week 12 | Week 4 | Week 12 |
| 0.375 mg dose vs. placebo | <0.001 | <0.001 | 0.036 | 0.002 |
| 0.27 mg dose vs. placebo | 0.034 | 0.026 | 0.194 | 0.012 |

These two sets of data clearly show that the doses of the invention surprisingly and unexpectedly efficiently treat menopause-related symptoms, namely the frequency and the severity of vasomotor symptoms.

Example 2

Frequency of Moderate to Severe Hot Flushes at Each Week

Table 2 presents summaries of the results of the endpoints of frequency of moderate to severe hot flushes at each week. Results were consistent with the primary efficacy results.

The group with the 0.375 mg dose achieved statistical significance at Week 2 and remained statistically significant through Week 12.

The group with the 0.27 mg dose achieved statistical significance at Week 4, then again at Week 7 and remained statistically significant through Week 12 with the noted exception of Week 10.

Thus, contrary to the teachings of the prior art, the doses of the invention are efficient at decreasing the frequency of vasomotor symptoms in menopausal women.

TABLE 2

Frequency of Moderate to Severe Hot Flushes Observed Case Analysis

| Week | Treatment | n | Mean (SD) | P-value vs. Placebo |
|---|---|---|---|---|
| Baseline | 0.375 mg dose | 113 | 12.50 (14.10) | |
| | 0.27 mg dose | 111 | 11.73 (4.33) | |
| | Placebo | 111 | 11.85 (7.25) | |
| Week 1 - Change from Baseline | 0.375 mg dose | 113 | −1.93 (4.93) | 0.639 |
| | 0.27 mg dose | 111 | −1.05 (3.70) | 0.522 |
| | Placebo | 110 | −1.54 (5.99) | |
| Week 2 - Change from Baseline | 0.375 mg dose | 113 | −4.36 (9.03) | 0.027 |
| | 0.27 mg dose | 108 | −2.97 (3.77) | 0.554 |
| | Placebo | 111 | −3.02 (7.44) | |
| Week 3 - Change from Baseline | 0.375 mg dose | 111 | −5.73 (11.64) | <0.001 |
| | 0.27 mg dose | 108 | −4.08 (4.18) | 0.098 |
| | Placebo | 109 | −3.36 (7.60) | |
| Week 4 - Change from Baseline | 0.375 mg dose | 108 | −6.91 (13.03) | <0.001 |
| | 0.27 mg dose | 105 | −4.63 (4.69) | 0.034 |
| | Placebo | 108 | −3.47 (8.02) | |
| Week 5 - Change from Baseline | 0.375 mg dose | 106 | −7.56 (14.10) | <0.001 |
| | 0.27 mg dose | 102 | −5.20 (4.63) | 0.118 |
| | Placebo | 106 | −4.29 (7.63) | |
| Week 6 - Change from Baseline | 0.375 mg dose | 105 | −7.83 (14.83) | <0.001 |
| | 0.27 mg dose | 100 | −5.62 (4.71) | 0.113 |
| | Placebo | 98 | −4.81 (8.26) | |
| Week 7 - Change from Baseline | 0.375 mg dose | 104 | −8.05 (14.97) | <0.001 |
| | 0.27 mg dose | 100 | −6.02 (4.61) | 0.026 |
| | Placebo | 96 | −4.43 (8.77) | |
| Week 8 - Change from Baseline | 0.375 mg dose | 103 | −8.49 (14.96) | <0.001 |
| | 0.27 mg dose | 99 | −6.02 (4.73) | 0.032 |
| | Placebo | 92 | −4.62 (9.42) | |
| Week 9 - Change from Baseline | 0.375 mg dose | 100 | −8.69 (15.22) | <0.001 |
| | 0.27 mg dose | 99 | −6.24 (4.86) | 0.041 |
| | Placebo | 93 | −4.71 (8.96) | |
| Week 10 - Change from Baseline | 0.375 mg dose | 99 | −8.47 (15.30) | <0.001 |
| | 0.27 mg dose | 96 | −6.29 (4.98) | 0.074 |
| | Placebo | 92 | −5.13 (8.46) | |
| Week 11 - Change from Baseline | 0.375 mg dose | 99 | −8.81 (15.29) | <0.001 |
| | 0.27 mg dose | 96 | −6.29 (4.81) | 0.033 |
| | Placebo | 91 | −4.85 (8.47) | |
| Week 12 - Change from Baseline | 0.375 mg dose | 99 | −8.76 (15.28) | 0.001 |
| | 0.27 mg dose | 93 | −6.19 (5.17) | 0.026 |
| | Placebo | 88 | −4.91 (8.87) | |

Note:
P-value from an Analysis of Covariance with treatment, center and baseline as terms in the model.

Example 3

Severity of Moderate to Severe Hot Flushes at Each Week

Table 3 presents summaries of the results of the endpoints of severity of moderate to severe hot flushes at each week. Results were consistent with the primary efficacy results.

The group with the 0.375 mg dose achieved statistical significance at Week 4 and remained statistically significant through Week 12.

The group with the 0.27 mg dose achieved statistical significance at Week 8 and remained statistically significant through Week 12.

Thus, contrary to the teachings of the prior art, the doses of the invention are efficient at decreasing the severity of vasomotor symptoms in menopausal women.

TABLE 3

Severity of Moderate to Severe Hot Flushes Observed Case Analysis

| Week | Treatment | n | Mean (SD) | P-value vs. Placebo |
|---|---|---|---|---|
| Baseline | 0.375 mg dose | 113 | 2.52 (0.23) | |
| | 0.27 mg dose | 111 | 2.52 (0.21) | |
| | Placebo | 111 | 2.52 (0.21) | |
| Week 1 - Change from Baseline | 0.375 mg dose | 113 | 0.00 (0.15) | 0.975 |
| | 0.27 mg dose | 111 | −0.02 (0.16) | 0.350 |
| | Placebo | 110 | 0.00 (0.12) | |
| Week 2 - Change from Baseline | 0.375 mg dose | 113 | −0.10 (0.28) | 0.260 |
| | 0.27 mg dose | 108 | −0.10 (0.34) | 0.347 |
| | Placebo | 111 | −0.06 (0.30) | |
| Week 3 - Change from Baseline | 0.375 mg dose | 111 | −0.19 (0.58) | 0.100 |
| | 0.27 mg dose | 108 | −0.21 (0.54) | 0.072 |
| | Placebo | 109 | −0.09 (0.46) | |
| Week 4 - Change from Baseline | 0.375 mg dose | 108 | −0.31 (0.67) | 0.036 |
| | 0.27 mg dose | 105 | −0.26 (0.59) | 0.194 |
| | Placebo | 108 | −0.15 (0.59) | |
| Week 5 - Change from Baseline | 0.375 mg dose | 106 | −0.35 (0.76) | 0.039 |
| | 0.27 mg dose | 102 | −0.29 (0.69) | 0.154 |
| | Placebo | 106 | −0.16 (0.54) | |
| Week 6 - Change from Baseline | 0.375 mg dose | 105 | −0.49 (0.90) | 0.034 |
| | 0.27 mg dose | 100 | −0.36 (0.82) | 0.291 |
| | Placebo | 98 | −0.24 (0.67) | |
| Week 7 - Change from Baseline | 0.375 mg dose | 104 | −0.67 (1.06) | <0.001 |
| | 0.27 mg dose | 100 | −0.40 (0.83) | 0.168 |
| | Placebo | 96 | −0.20 (0.63) | |
| Week 8 - Change from Baseline | 0.375 mg dose | 103 | −0.59 (0.99) | 0.001 |
| | 0.27 mg dose | 99 | −0.46 (0.87) | 0.019 |
| | Placebo | 92 | −0.18 (0.60) | |
| Week 9 - Change from Baseline | 0.375 mg dose | 100 | −0.77 (1.08) | <0.001 |
| | 0.27 mg dose | 99 | −0.60 (1.03) | 0.010 |
| | Placebo | 93 | −0.23 (0.62) | |
| Week 10 - Change from Baseline | 0.375 mg dose | 99 | −0.76 (1.06) | 0.005 |
| | 0.27 mg dose | 96 | −0.58 (0.98) | 0.039 |
| | Placebo | 92 | −0.30 (0.71) | |
| Week 11 - Change from Baseline | 0.375 mg dose | 99 | −0.89 (1.14) | 0.003 |
| | 0.27 mg dose | 96 | −0.66 (1.06) | 0.045 |
| | Placebo | 91 | −0.31 (0.74) | |
| Week 12 - Change from Baseline | 0.375 mg dose | 99 | −0.90 (1.15) | 0.002 |
| | 0.27 mg dose | 93 | −0.70 (1.08) | 0.012 |
| | Placebo | 88 | −0.34 (0.80) | |

Note:
P-value from an Analysis of Covariance with treatment, center and baseline as terms in the model.

Example 4

Vulvar and Vaginal Atrophy

Table 4 presents a summary of moderate to severe symptoms of vulvar and vaginal atrophy at baseline and endpoint. The 0.375 mg dose and 0.27 mg dose groups achieved statistical significance at endpoint for the observed case analysis (p=0.012 and p=0.016, respectively). These results show that unexpectedly, the doses of the invention are efficient in treating menopause-related symptoms, namely vulvar and/or vaginal atrophy.

TABLE 4

Moderate to Severe Symptom of Vulvar and Vaginal Atrophy Observed Case Analysis

| Week Rating | 0.375 mg dose (N = 114) | 0.27 mg dose (N = 115) | Placebo (N = 113) | Comparison Treatment | P-value vs. Placebo |
|---|---|---|---|---|---|
| Baseline | | | | | |
| Moderate | 26 (22.8%) | 21 (18.3%) | 28 (24.8%) | | |
| Severe | 18 (15.8%) | 16 (13.9%) | 22 (19.5%) | | |
| Endpoint | | | | | |
| None | 10 (8.8%) | 6 (5.2%) | 9 (8.0%) | 0.375 mg dose | 0.012 |
| Mild | 17 (14.9%) | 15 (13.0%) | 5 (4.4%) | 0.27 mg dose | 0.016 |
| Moderate | 9 (7.9%) | 10 (8.7%) | 21 (18.6%) | | |
| Severe | 6 (5.3%) | 5 (4.3%) | 10 (8.8%) | | |

Note:
P-value from Fisher's Exact Tests with the Bonferroni-Holm adjustment applied.

Example 5

Plasma Concentrations of Estradiol (E2) and Unconjugated Estrone (E1)

The geometric mean values of plasma concentrations of E2 (estradiol), E1 (unconjugated estrone), and the E2/E1 ratio for both doses are summarized in the Table 5 below.

TABLE 5

Geometric Mean Concentrations of E2 and E1 and the E2/E1 Ratio

| | 0.375 mg estradiol dose | | | | 0.270 mg estradiol dose | | | |
|---|---|---|---|---|---|---|---|---|
| | N | E2 (pg/mL) | E1 (pg/mL) | E2/E1 | N | E2 (pg/mL) | E1 (pg/mL) | E2/E1 |
| Baseline | 98 | 3.7 | 17.7 | 0.2 | 95 | 4.2 | 20.7 | 0.2 |
| Week 4 | 34 | 18.3 | 39.6 | 0.5 | 39 | 14.2 | 35.5 | 0.4 |
| Week 8 | 46 | 15.8 | 37.2 | 0.4 | 44 | 15.6 | 34.0 | 0.5 |
| Week 12 | 36 | 21.4 | 44.9 | 0.5 | 36 | 14.0 | 37.8 | 0.4 |

Over the 12-week treatment period, the plasma E2 concentrations for the 0.375 mg dose ranged from 16 to 21 pg/mL.

The foregoing data indicate the following:

With respect to frequency of moderate to severe hot flushes, statistical significance was achieved at Week 2 for the 0.375 mg dose, and at Week 4 for the 0.27 mg dose. A statistically significant effect on the severity of moderate to severe hot flushes was noted at Weeks 4 and 8 for the two doses, respectively. Both the 0.375 mg dose and the 0.27 mg dose had statistically significant improvement in moderate to severe symptoms of vulvar and vaginal atrophy. Thus, contrary to the teachings from the prior art, the (low) doses of the invention alleviate menopause-related symptoms.

What is claimed is:

1. A method of alleviating at least one menopause-associated symptom in a female patient in need thereof, comprising topically administering to said patient an amount of a composition comprising estradiol effective to administer an estradiol dose of about 0.25-0.42 mg/day, wherein the composition is a hydroalcoholic gel that comprises (i) about 0.025-0.035% (w/w) estradiol, (ii) about 0.1-1.5% (w/w) gelling agent, (iii) about 30-50% (w/w) C2-C6 alcohol, and (iv) water.

2. The method of claim 1, wherein the estradiol dose is about 0.35-0.40 mg/day.

3. The method of claim 1, wherein the estradiol dose is about 0.375 mg/day.

4. The method of claim 1, wherein the menopause-associated symptom is selected from the group consisting of vasomotor symptoms, vulvar atrophy, vaginal atrophy, and combinations thereof.

5. The method of claim 1, wherein the menopause-associated symptom is hot flushes.

6. The method of claim 1, wherein the method is effective to achieve at least one effect selected from the group consisting of decreasing the severity of vasomotor symptoms, decreasing the frequency of vasomotor symptoms, decreasing the severity of vulvar atrophy, decreasing the severity of vaginal atrophy, and combinations thereof.

7. The method of claim 1, wherein the gelling agent comprises at least one polyacrylic acid.

8. The method of claim 7, wherein the gelling agent comprises at least one carbomer.

9. The method of claim 1, wherein the composition comprises (i) about 0.03% (w/w) estradiol, (ii) about 0.5-1% (w/w) polyacrylic acid polymer, (iii) about 40% (w/w) absolute ethanol, and (iv) water.

10. The method of claim 1, wherein the composition is a hydroalcoholic gel that comprises (i) about 0.03% (w/w) estradiol; and (ii) about 40% (w/w) absolute ethanol, wherein said composition has a Brookfield viscosity at 20° C. of between 30-120 Pa·s.

11. The method of claim 10, wherein said Brookfield viscosity is 35-100 Pa·s.

12. The method of claim 10, wherein said Brookfield viscosity is 50-60 Pa·s.

* * * * *